(12) United States Patent
Yun et al.

(10) Patent No.: US 7,400,704 B1
(45) Date of Patent: *Jul. 15, 2008

(54) HIGH RESOLUTION DIRECT-PROJECTION TYPE X-RAY MICROTOMOGRAPHY SYSTEM USING SYNCHROTRON OR LABORATORY-BASED X-RAY SOURCE

(75) Inventors: Wenbing Yun, Walnut Creek, CA (US); David Dean Scott, Oakland, CA (US); David R. Trapp, Tracy, CA (US); Frederick William Duewer, Albany, CA (US); Yuxin Wang, Arlington Heights, IL (US)

(73) Assignee: Xradia, Inc., Concord, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/537,806

(22) Filed: Oct. 2, 2006

Related U.S. Application Data

(63) Continuation of application No. 11/035,749, filed on Jan. 14, 2005, now Pat. No. 7,130,375.

(60) Provisional application No. 60/536,385, filed on Jan. 14, 2004.

(51) Int. Cl.
*G01N 23/20* (2006.01)
*A61B 6/08* (2006.01)
*H05G 1/00* (2006.01)

(52) U.S. Cl. .......................... 378/79; 378/205; 378/209
(58) Field of Classification Search .................. 378/70, 378/73, 79–85, 98.8, 205, 208, 209; 250/370.09, 250/370.11
See application file for complete search history.

(56) References Cited

U.S. PATENT DOCUMENTS

| | | | | |
|---|---|---|---|---|
| 4,833,698 | A * | 5/1989 | Flannery et al. | 378/19 |
| 5,245,648 | A * | 9/1993 | Kinney et al. | 378/43 |
| 6,055,292 | A * | 4/2000 | Zeller et al. | 378/21 |
| 6,104,776 | A * | 8/2000 | Oikawa | 378/22 |
| 6,249,566 | B1 * | 6/2001 | Hayashi et al. | 378/85 |
| 6,831,962 | B2 | 12/2004 | Lentfer | |

* cited by examiner

*Primary Examiner*—Irakli Kiknadze
(74) *Attorney, Agent, or Firm*—Houston Eliseeva LLP

(57) ABSTRACT

A projection-based x-ray imaging system combines projection magnification and optical magnification in order to ease constraints on source spot size, while improving imaging system footprint and efficiency. The system enables tomographic imaging of the sample especially in a proximity mode where the same is held in close proximity to the scintillator. In this case, a sample holder is provided that can rotate the sample. Further, a z-axis motion stage is also provided that is used to control distance between the sample and the scintillator.

15 Claims, 7 Drawing Sheets

HIGH RESOLUTION DIRECT-PROJECTION TYPE X-RAY MICROTOMOGRAPHY SYSTEM USING SYNCHROTRON OR LABORATORY-BASED X-RAY SOURCE

RELATED APPLICATIONS

This application is a continuation of copending U.S. application Ser. No. 11/035,749, filed on Jan. 14, 2005, which claims the benefit under 35 USC 119(e) of application Ser. No. 60/536,385 filed on Jan. 14, 2004, both of which are incorporated herein by this reference in their entirety.

BACKGROUND OF THE INVENTION

Since its discovery, the ability of x rays to penetrate through material has been exploited extensively, such as in non-invasive and non-destructive imaging in medical and industrial applications.

For example, a number of manufacturers have developed imaging tools for failure analysis of integrated circuit (IC) packaging that take advantage of the penetrating power of hard x rays with tens to hundreds of kilo electron-Volts (keV) energy. These x-ray inspection tools typically provide resolutions on the order of tens of micrometers. This is sufficient for inspecting most large features in IC packages. They provide sample mounting mechanisms and multi-axis motion control to allow the operator to translate, zoom, and tilt the sample with a joystick while observing the image in real time. These systems are widely deployed in packaging failure analysis (FA) labs.

In addition, with increasing feature density and complexity, two-dimensional (2 D) x-ray micrographs tend to contain too much overlapping information for the operators to interpret, necessitating the inclusion of a quantitative third dimensional (3 D) imaging capability in the FA tools.

Many x-ray inspection tool manufacturers have developed systems to meet the IC manufacturer's needs. The following is a brief overview of these x-ray inspection tools.

Some current commercial tools are arranged in a relatively simple projection geometry, in which the radiation produced by an x-ray source is allowed to penetrate the sample, and the transmitted radiation is collected by the detector. With this setup, the geometrical magnification of the system is:

$$M = \frac{L_s + L_d}{L_s}, \quad (1)$$

where, $L_s$ is the source to sample distance and the $L_d$ is the sample to detector distance. As a result, the achievable resolution of these systems can be derived, being roughly:

$$\delta \geq \frac{M-1}{M} s, \quad (2)$$

where s is the size of the x-ray source spot.

From this relationship, in order to achieve high resolution, one should make M as close to 1 as possible. In the limit where M=1, the sample plane overlaps the detector plane, which is the geometry of contact printing mode.

Contact printing, however, requires a detector with high enough resolution to sample the contact image, since with the magnification close to one. Thus, the detector resolution must be on par with the sample feature to be resolved.

In the absence of such a high resolution detector, an alternative imaging mode is to increase the geometric magnification so that the features in the sample are magnified sufficiently such that they can then be sampled with a detector with coarse resolution. In this projection mode, M>1, the resolution is about the same as the source size. Thus, high resolution requires a source with very small spot size.

SUMMARY OF THE INVENTION

Non-destructive packaging inspection requires x rays with sufficient energy to penetrate through a complete device without deprocessing. X ray sources with 100-150 keV electron bombardment energy are used in most commercial systems. To achieve micrometer scale resolution in a contact printing mode, a scintillated detector with microscope objective coupling is required. The radiation passing through the sample is detected by a single crystal scintillator to convert the x-ray image to a visible light image, which is then imaged to a camera by an objective lens. To reach micrometer scale resolution, the objective lens must have sufficiently high numerical aperture of at least 0.25. This high numerical aperture restricts the depth of field to tens of micrometer. Therefore, the scintillator must be made thinner than tens of micrometers in order to achieve the desired resolution. This thin scintillator typically absorbs only about 10-20% of the incoming radiation, therefore reducing the efficiency and the throughput.

With the projection mode, on the other hand, the detector can be of coarse resolution with good efficiency, but the x-ray source spot size must be kept less than one micrometer. Electrons with 100 keV energy bombarding an x-ray target material typically have mean free path of tens to hundreds of micrometers. The x-ray generation volume of a target is approximately that of the electron focal spot near the surface, but balloons to tens to hundreds of micrometers deeper into the target. To keep the spot size to one micrometer, one must either lower the electron acceleration voltage, or use a thin film target with less than a micrometer thickness instead of a solid target. Lowering the acceleration voltage makes the x rays less penetrating and is acceptable only in special cases, such as, for example, when the sample can be cut into small pieces to be imaged. Using a thin film target allows x rays to be generated only near the surface and avoid most of the x-ray generation volume. This clearly causes a severe efficiency loss since at 100 keV, no more than a few percent of the x rays are generated near the surface.

The present invention is directed to a projection-based x-ray imaging system that combines projection magnification and optical magnification in order to ease constraints on source spot size, while improving imaging system footprint and efficiency.

The present invention is also directed to an x-ray imaging system that enables tomographic imaging of the sample especially in a proximity mode where the sample is held in close proximity to the scintillator. In this case, a sample holder is provided that can rotate the sample. Further, a z-axis motion stage is also provided that is used to control distance between the sample and the scintillator.

In general, according to one aspect, the invention features an x-ray imaging system. This imaging system comprises an x-ray source generating a diverging x-ray beam. This diverging x-ray beam is characteristic of projection systems since the diverging beam enables magnification in the system's x-ray stage.

The imaging system also comprises an optical stage. This stage includes a detector such as a film or camera detector, such as one based on a charge coupled device (CCD). A magnification lens is also provided in the optical stage for imaging the optical signal of the scintillator onto the detector.

In the preferred embodiment, the spot size of the x-ray source is relatively large for a high resolution projection imaging system. This is because in the present invention, a hybrid system is provided that has both x-ray and optical magnification. As a result, the spot size of the x-ray source is between 1 and 10 micrometers in diameter. This large spot size can be used while still allowing for resolution of 1 micrometer and less.

In the preferred embodiment, the magnification for the entire imaging system is distributed between the projection x-ray stage and the optical stage. In the preferred embodiment, the magnification of the optical stage is between 1 and 20 times. The magnification of the x-ray stage is between 1 and 10 times. Preferably, the magnification of the x-ray is relatively small, less than 2 times. This system provides for relatively high resolutions for a projection system while also decreasing the design constraints associated with the x-ray stage, thereby improving efficiency and the performance of the system.

In the preferred embodiment, the imaging system operates in a proximity mode in which the sample is held relatively close to the scintillator. In the preferred embodiment, the distance between the sample and the scintillator is between 1 and 50 millimeters. Preferably, it is between 1 and 10 millimeters.

In general, according to another aspect, the invention features an x-ray imaging system. This system also comprises a projection x-ray stage. This portion includes an x-ray source that generates a diverging x-ray beam. Further, a scintillator is provided for converting the diverging x-ray beam, after its interaction with the sample, into an optical signal. A sample holder is further provided for holding and positioning the sample in proximity to the scintillator. This sample holder comprises a rotation motion stage for rotating the sample in the x-ray beam. A z-axis motion stages are further provided for adjusting a distance between the source and sample and the sample and scintillator.

In the preferred embodiment, a further z-axis motion stage moves the scintillator.

In the preferred embodiment, the system further comprises a source motion stage for moving the source in the direction as perpendicular to an axis of the x-ray beam. This allows for the positioning of the x-ray beam. Further, a y-axis sample motion stage is preferably provided for adjusting the vertical height of the sample in the x-ray beam.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
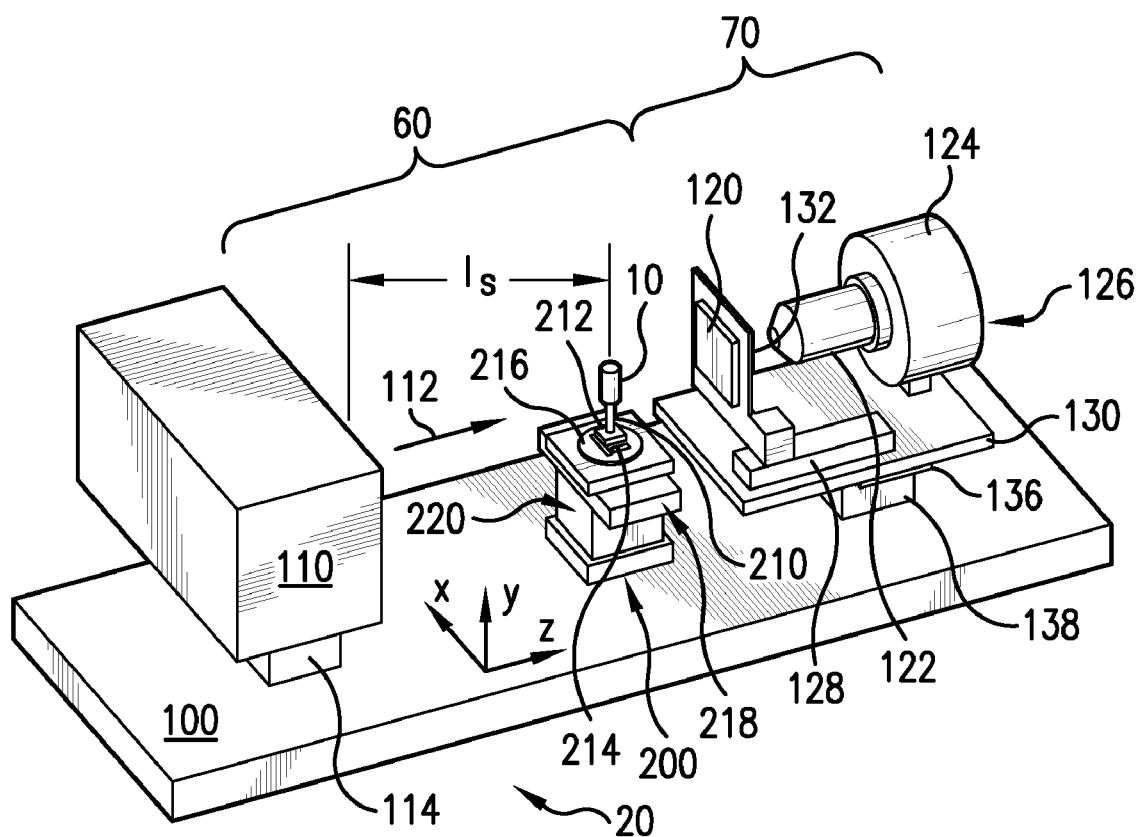
FIG. 1 is a schematic perspective view of an x-ray imaging system according to the present invention.

FIG. 1 illustrates an x-ray imaging system that has been constructed according to the principles of the present invention.

Specifically, the x-ray imaging system 20 comprises an optical table 100. This provides a stable, planar surface on which the components of the imaging system 20 are secured.

An x-ray source 110 is secured to one end of the optical table 100. It generates an x-ray beam 112, which is typically a diverging x-ray beam as is common in these x-ray projection systems.

In one example, the x-ray source 110 is a rotating-anode type, with a tungsten target, but in other embodiments, the target comprises molybdenum, gold, platinum, silver, or copper.

In still other examples, the source 110 is a synchrotron radiation x-ray source.

In the preferred embodiment, the x-ray source 110 can be moved relative to the optical table 100. Specifically, an x-axis source motion stage 114 is preferably provided in order to adjust the position of the x-ray source, and consequently the x-ray beam 112 along the x-axis relative to the optical table 100.

The x-ray beam 112 is used to illuminate a sample 10. This is the sample 10 on which x-ray imaging is performed. In one example, the sample 10 is a packaged integrated circuit. The x-ray imaging process allows for the non-destructive imaging of the internal features of this packaged integrated circuit in order to, for example, test the packaging process.

According to the invention, the x ray stage 60 has a projection configuration. Thus, there are no x ray element that focuses the x ray beam between the source and the sample and between the sample and detector.

According to one aspect of the invention, a sample holder 200 is provided in order to position the sample 10 in the x-ray beam 112 relative to the optical table platform 100. Specifically, in the illustrated embodiment, the sample 10 is held on a sample mount 210. This in turn projects from a mount base 212. This base 212 translates in the x-z plane under control of an x-z sample motion stage 214. This allows for fine positioning of the sample 10 in the x-z plane.

A sample rotation stage 216 is used to rotate the x-z sample motion stage 214 and thus rotate the sample 10 in the x-ray beam 112, around an axis of rotation extending parallel to the y-axis. This rotation is important when performing tomographic reconstruction of the internal structures of the samples.

In the preferred embodiment, an x-axis sample motion stage 218 is further provided. This x-axis sample motion stage 218 provides for relatively large or gross positioning of the sample 10 along the x-axis and in the x ray beam. For example, this allows for the loading of the sample into the system 20.

Moreover, in the preferred embodiment, a y-axis sample motion stage 220 is preferably also provided. This allows for the y-axis adjustment of the sample 10. Specifically, the y-axis stage connects the x-axis sample motion stage to the bench 100. This y-axis motion stage 220 allows for the height adjustment of the sample in the x-ray beam 112 and relative to the top of the optical table 100.

The x ray stage 60 of the imaging system 20 ends in a scintillation screen or scintillator 120. This converts the x-rays of the x-ray beam 112 into an optical signal. This optical signal is then received by the optical stage 70 for further magnification according to the present invention and detection in a camera or film based detector.

In more detail, the x ray beam after interaction with the sample is converted into an optical signal in the scintillator material of the scintillator screen 120.

A visible light magnification lens system 122 then captures the optical signal emitted from the scintillation screen and forms an image of this signal onto a CCD detector 124.

In order to ensure an imaging condition on the detector such as the CCD detector 124, a z-axis scintillator motion stage 128 is preferably provided in order to adjust a distance between the scintillation screen and the magnification lens system 122. Specifically, in the illustrated example, both the magnification lens/camera assembly 126 and a z-axis scintillator motion stage 128 are secured to an optical stage sub assembly bench 130. The scintillation screen 120 is supported on a frame 132 that is moved by the z-axis scintillator motion stage 128 in order to thereby adjust the distance between the scintillation screen 120 and the magnification lens system 122.

In order to provide for further alignment between the x ray stage 60 and the optical stage 70, an x-axis optical motion stage 136 is preferably provided. This allows the movement of the optical stage bench 130 in the x-axis direction. An y-axis optical motion stage 138 is preferably provided for moving the optical stage bench 130 and thus the optical stage 70 in the y-axis direction or vertical to the optical bench 100.

Different materials can be used for the scintillator 120 such as Cesium Iodide (CsI) or Cadmium Tungstate ($CdWO_4$).

In one configuration, the thickness of scintillator 120 is between 10 μm and 1 millimeters (mm). The optical stage 70 then provides magnification of about 2 times.

In another implementation, thickness of scintillator 120 is between 10 μm and 500 μm, with the optical stage 70 providing a magnification of 5×.

In a still further implementation, a thinner scintillator 120 of between 5 μm and 250 μm is used with the optical stage 70 providing a magnification of 10×.

Also a thickness of 2 μm to 200 μm and an optical stage providing a magnification of 20× can be used. In still other examples, optical stage provides for magnification of about 50× or less.

Preferably, the source to sample distance $l_s$ is between 5 centimeters (cm) to 50 cm. One sample to detector distance $l_d$ is between 5 cm to 20 cm.

By rotating the sample 10 using sample rotation stage 216 and collecting multiple images, tomography can be used to generate a 3 D image. Applicable tomography algorithms include the filtered backprojection method. In others, the tomography algorithm is the algebraic reconstruction technique (generally abbreviated as ART) and it derivatives or the Fourier inversion technique.

This imaging system 20 is used for imaging semiconductor chip packaging and associated components, in one application. It can also be used to image electronic circuit boards and micro-electro-mechanical system (MEMS) devices. Small animals and geological samples can also be imaged.

Failures such as shorts and broken lines can often be observed with 2 D real-time systems by directly imaging the suspected area or by tracking problematic lines identified from electrical testing. With some complex packaging types, 2 D images often contain too many overlapping features for positive identification and 3 D tomographic images are very valuable in providing a clear identification. Shorts in molding compounds caused by electro-migration or chemical reactions can often be imaged. This type of defect results when metal from the wire dissolves into the molding compound. They are often more difficult to see than direct wire contact shorts due to lower contrast, but can be effectively identified with x-ray techniques when combined with careful electrical testing.

Voids in solder bumps are usually visible by imaging with 2 D real-time systems. To accurately determine the location, size, and distribution of voids, however, a 3 D tomography system is invaluable. Wicking is difficult to identify from 2 D images, but can be easily observed from virtual cross-sections of a 3 D tomographic reconstruction.

Non-destructive x-ray imaging is an ideal tool for inspecting the contact surfaces to the die. Also, there can be small particles and clusters trapped in the substrate. They typically range from a few micrometers to tens of micrometers in size. Because of their small size, a high-resolution tool is required to image them, and since they often have very low contrast, they also tend to be very difficult to find from individual 2 D images, which contain many overlapping features. The shorts represent such a case where the fault location was carefully determined from electrical testing and the copper particle was isolated between two bond wires. In more difficult cases where the particle is located between layers and among complex circuits, a 3 D imaging system will be required to resolve the small particles in the depth direction. The operator must then carefully go through the 3 D data set to find the particle.

Underfill entrapments typically result from particles being trapped in the solder bumps or other circuit structures. Since these particles usually have lower density than the solder material, they typically have a similar appearance as voids, but with irregular shapes. They can be observed with either 2 D real-time or 3 D tomographic imaging.

Most via delamination defects are very difficult to image with x-ray techniques because they typically occur under a solder bump with the crack parallel to the chip surface, hence the crack is blocked by the x-ray opaque solder and is only visible at extremely large tilt angles. However, by allowing full 180 degree sample tilt during tomographic data acquisition, x ray analysis is possible. Using high-tilt angle projections, it is usually possible to produce a high resolution 3 D tomographic image that reveals the delamination crack. High resolution is essential since these cracks are often quite narrow, with a width of no more than a few micrometers at the widest point.

Figure 2:
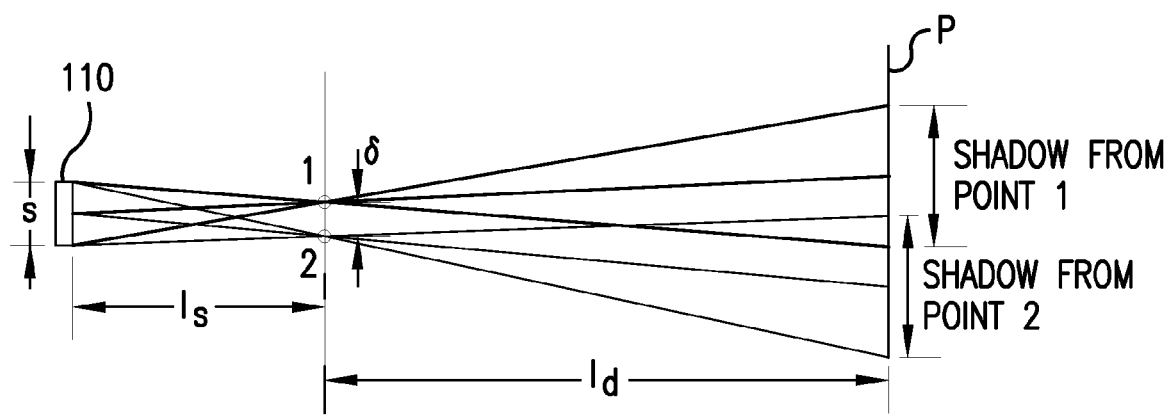
FIG. 2 illustrates the geometry of a projection imaging system showing the relationship between spot size and resolution.

FIG. 2 illustrates the relevance of the spot size s of the source 110 to system resolution.

Consider a projection imaging system having an x-ray source 110 with lateral size s, two point objects 1 and 2, and a detector plane p. The separation between the source 110 and the objects is $l_s$, and the separation between the object and the detector plane is $l_d$.

Each point casts a shadow on the detector plane with the size $(l_d/l_s)s$. This is essentially the point spread function, which is:

$$psf = \frac{l_d}{l_s}s.$$

The magnification can be defined as the distance between the center of the shadows:

$$M = \frac{l_s + l_d}{l_s}.$$

Ignoring the diffraction effect, we can use the criteria that the two point objects are resolved if the center of the object does not fall into the shadow of the other. That is:

$$M \Box \delta \geq psf$$

$$\left(\frac{l_s + l_d}{l_d}\right)\delta \geq \frac{l_d}{l_s}s$$

Therefore the resolution limit determined by the imaging geometry is:

$$\delta \geq \frac{\frac{l_d}{l_s}}{1 + \frac{l_d}{l_s}}s, \text{ or } \delta \geq \frac{M-1}{M}s.$$

A few extreme cases:

Contact printing: $M \approx 1$, then $\delta = 0$. That is, infinitely high resolution can be achieved in contact printing mode. In practice the system resolution is only determined by the detector resolution.

Projection imaging: $l_d \gg l_s$, and $M \gg 1$, then $\delta \approx s$. In this mode, the system resolution is limited by the source size. If the detector can sample the image at sufficiently high resolution, the system resolution is approximately that of the source size. It is never worse than the source size.

Figure 3:
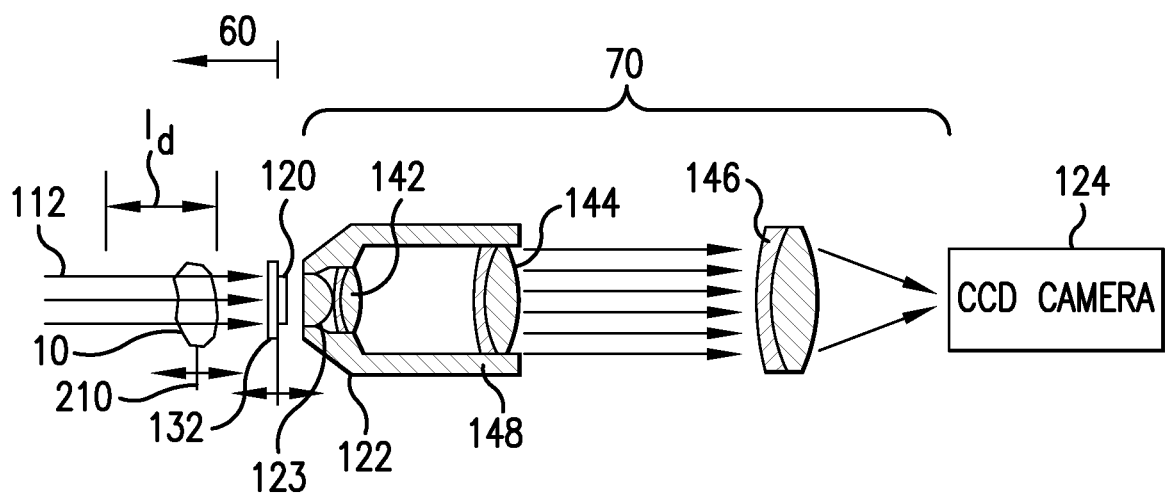
FIG. 3 is a side cross-sectional view of a scintillated optical stage including a camera.

FIG. 3 illustrates details of the x-ray stage 60 and the optical stage 70 and specifically the interface between these two stages.

The incoming x-ray beam 112 passes through the sample 10 and is received by the scintillator 120. The light, usually, visible, from the scintillator is then magnified by visible light magnification lens system 122, which includes a magnification lens 123 that is held within a housing 148. Two couplets 142, 144, are used to condition the optical signal. A final tube lens couplet 146 forms an image on the CCD camera 124.

According to the preferred embodiment, the imaging system operates in a proximity mode. The characteristic of this proximity mode is the distance between the sample 10 and the scintillator 120. Specifically, in the preferred embodiment, the distance Id between the sample 10 and the scintillator is relatively small. Specifically, it is between 1 and 50 millimeters. Ideally, it is smaller, however, between 1 and 10 millimeters.

Since this proximity mode is used as the sample 10 is rotated for tomographic reconstruction, it may often come into mechanical conflict with the scintillator 120 or the scintillator frame 132. As a result, the z-axis motion stages can be used to move the sample physically away from the scintillation screen 120 to enable its complete rotation as required in tomographic reconstruction.

In the preferred embodiment, the source size is relatively large for an imaging system providing 1 micrometer or better resolution. Specifically, the source size is between 1 and 10 micrometers. Preferably, it is about 2 micrometers in diameter or its lateral extent s. Thus, relatively inexpensive high efficiency sources can be used since the source spot size is relatively large.

In the preferred embodiment, the optical magnification stage 70 provides for between 1 and 20 times magnification. Preferably, the x-ray stage provides relatively small magnification compared to other projection systems. Specifically, the x-ray stage provides between 1 and 10 times magnification. Preferably, the x-ray stage only provides up to 2 times magnification.

Figure 4:
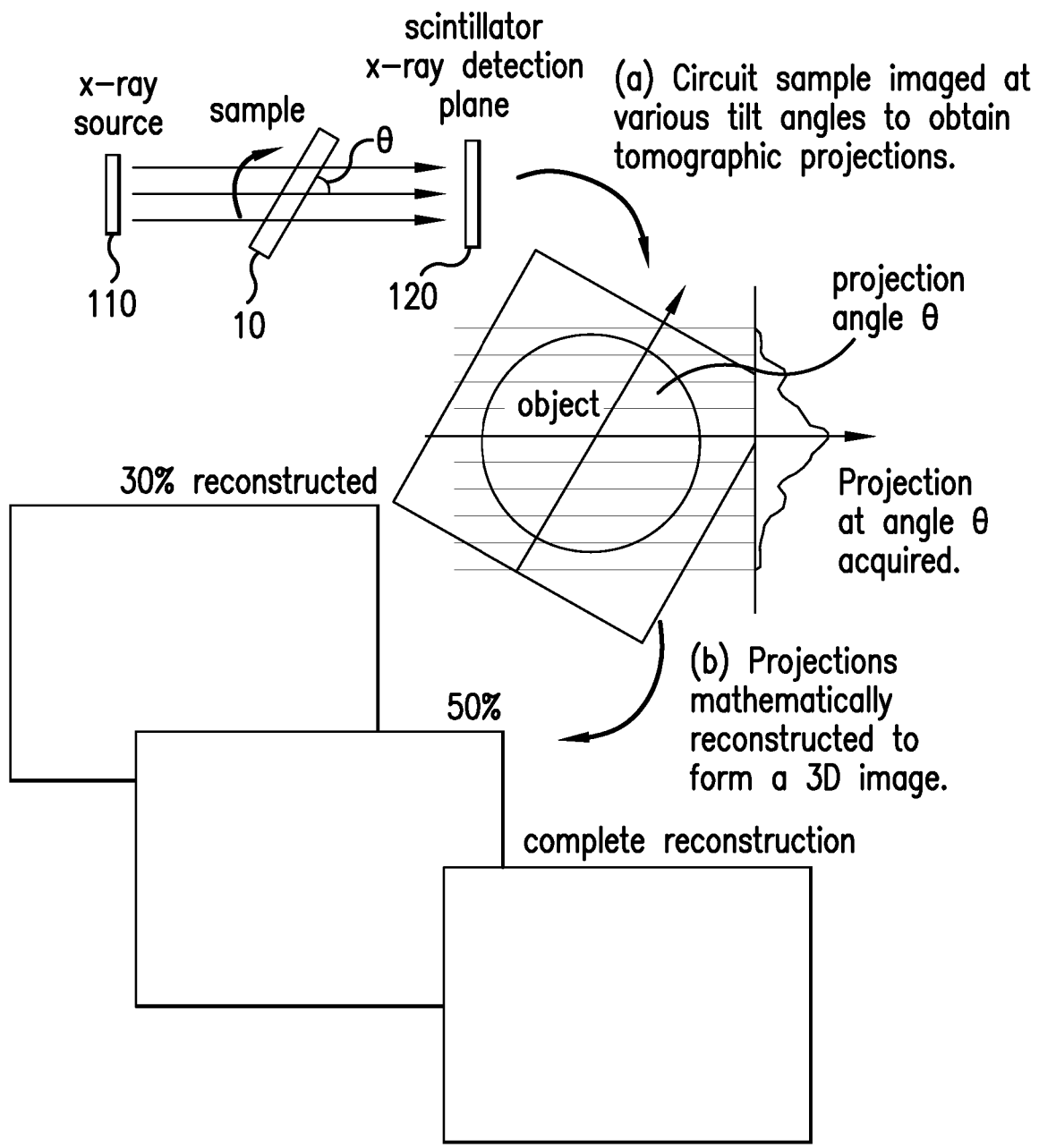
FIG. 4 illustrates the tomographic imaging and reconstruction process.

The process of tomographic imaging is illustrated in FIG. 4. The sample 10 is mounted on a rotation stage, and images are acquired at many tilt angles as the sample is rotated to collect the tomographic projections, such as P(θ). The projections are the integrated linear attenuation through the sample. Then the Fourier Slice Theorem states that the for each plane perpendicular to the rotation axis, the Fourier transform of P(θ) is equal to the Fourier transform of this plane along the θ direction (or more specifically its attenuation values). Therefore, if projections are acquired at many angles, one can fill the Fourier transform space of this plane and use an inverse Fourier transform to obtain the real value of the sample.

FIG. 4 shows the result when 30% (410), 50% (412), and finally all the projections (414) are summed into the reconstruction process.

During the tomographic data reconstruction, it is critical that the effective center of the rotation is placed at the center of the projection images. A three-step process is typically used to achieve this alignment:

The rotation axis of the rotation center is first identified. This is often done with the aim of an alignment target, such as a small sphere or BB ball. Take images at 0 degree and 180 degree rotation angle, the rotation axis should be located exactly half way between the target positions in these two images. This determines the rotation axis position in x. Move the x-axis on top of the rotation axis to this center position. Takes images at 90 and 270 degrees to determine the z center position. This step places the alignment target at the rotation axis.

The alignment target is then moved to the center of the image field by moving the x and y stages. This places the rotation axis at the center of the image field. One could also move the detector and source x and y stages to achieve this alignment.

Finally, Pitch and roll adjustments are made. Here, move the alignment target to the edge of the image field with the x-z stages on top of the rotation stage. Take images at 0, 90, 180, and 270 degrees. Calculate the pitch and roll angular errors of the rotation axis and make corrections by adjusting the relative height of the source and detector, by shimming, or control of the motion stages.

After the alignment is achieved, all stages except for the motion above the rotation axis should remain fixed and the sample should be moved by the stages above the rotation axis only.

Figure 5:
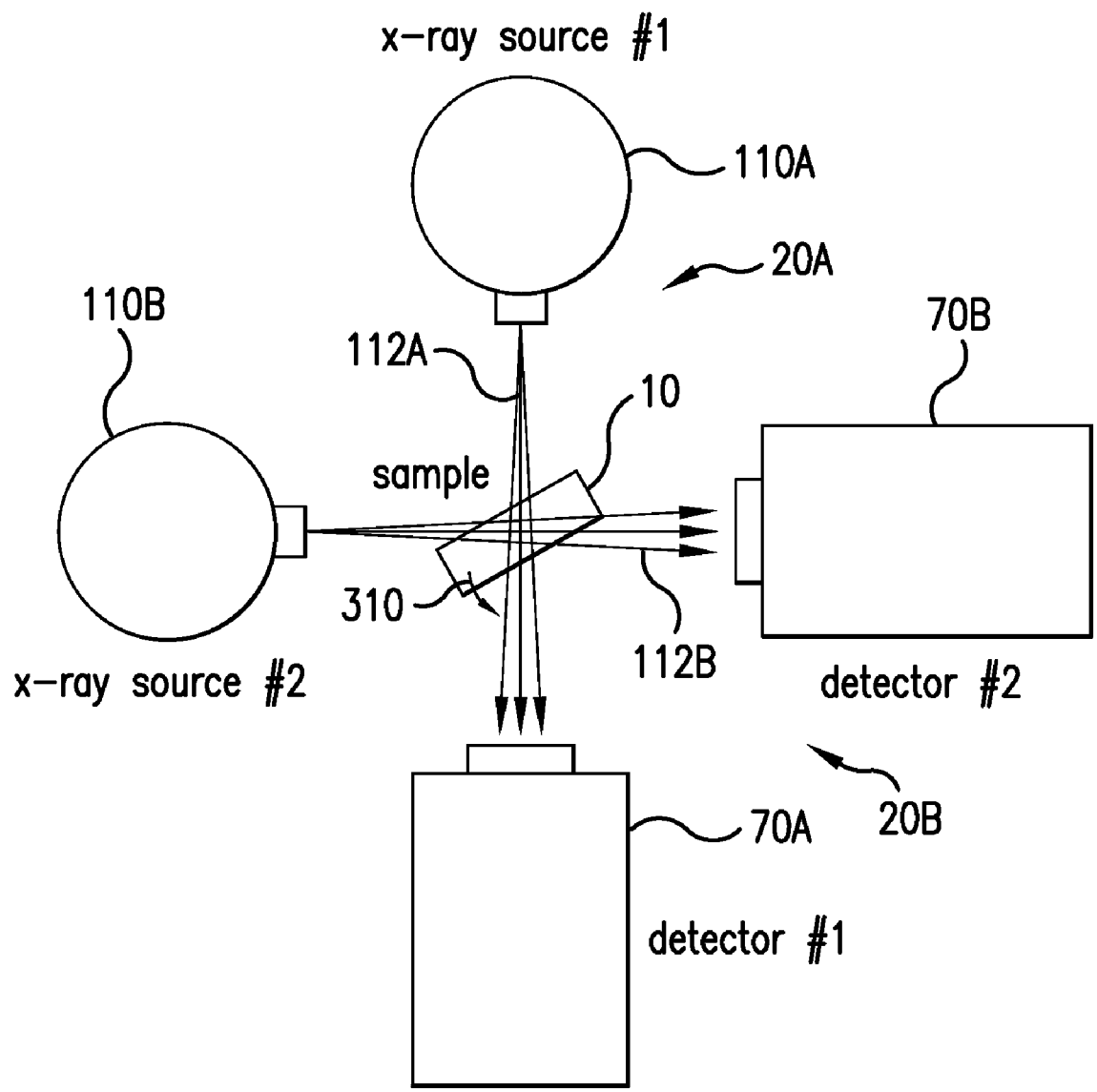
FIG. 5 illustrates an imaging system including two dual x-ray source and detectors systems that operate to simultaneously image a single sample.

FIG. 5 illustrates a system having a dual imaging system comprising two of the imaging systems 20 as described in FIG. 1, which are placed at an angle with respect to each other. Each imaging system 20A, 20B has a source for illuminating a single sample 10. Specifically, a first x-ray source 110a creates a first divergent beam 112a. A second x-ray source 110b similarly creates a second diverging x-ray beam 112b.

The first x-ray beam 112a, after interacting with the sample 10 is detected by a first detector, comprising a scintillator and optical assembly 70a. Similarly, the second diverging x-ray beam 112b is detected by a second detector comprising a scintillator and optical assembly 70b. This system provides for, in one example, a faster tomographic reconstruction of the structures within the sample 10. Specifically, as the sample is rotated, see arrow 310, both detectors can detect the corresponding x-rays in order to correct the node to fill the tomographic reconstruction space.

Figure 6:
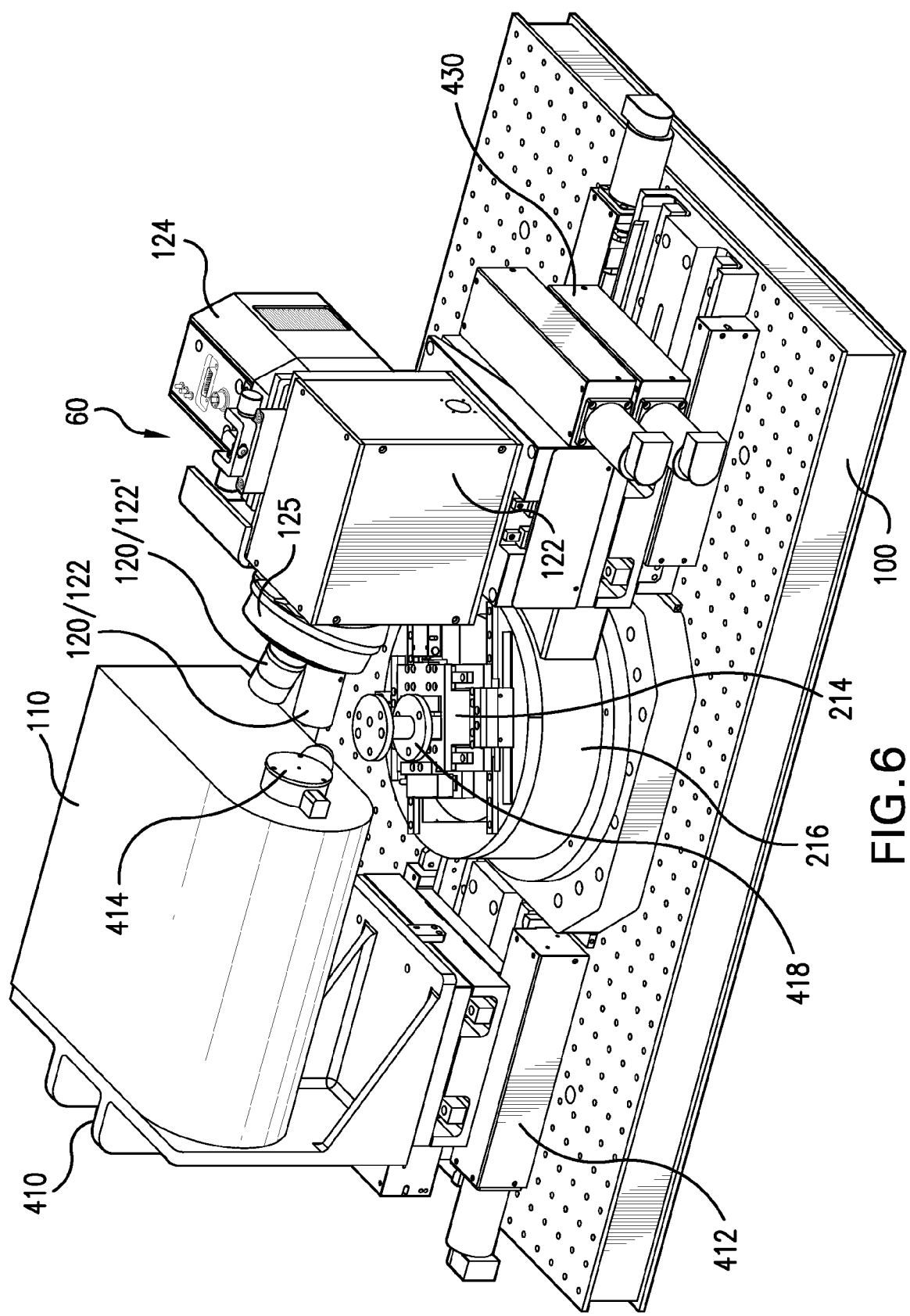
FIG. 6 is a scale perspective view illustrating the x-ray imaging system according to another embodiment.

FIG. 6 is a perspective view showing another embodiment of the x-ray imaging system. In this example, an x-ray source 110 is held on a support bracket 410. This support bracket 410 connects the x-ray source 110 to the bench 100 via a z-axis source motion stage 412. The x-ray beam is emitted from the source 110 via an x-ray aperture 114 to be transmitted through a sample that is held on the sample mount 418.

The z-axis source motion stage 412 enables control of the source sample distance $l_s$, which in important for controlling magnification in the x ray stage.

The x-ray signal is them received by the scintillator and microscope objective lens assemblies 120/122. It is then detected by the CCD camera 124. In this example, the magnification lens system 122 and camera 124 are held on an x-y-z linear motion optical assembly stage 430. This provides for the smooth positioning of the scintillator and optical stage 60 in three dimensions relative to the sample. Most importantly, it provides for z axis positioning of the detector and specifically scintillator 120 relative to the sample 10 to thereby dictate distance $l_d$, which controls magnification in conjunction with distance $l_s$. In summary, z-axis motion stages 412, 430 enable the adjustment of a source-to-sample distance and a sample-to-detector distance.

In one embodiment, second scintillator/optical system 120/122' is provided. It may have different scintillator material and/or scintillator thickness. Thus, the detector system has multiple scintillator/lens assemblies with magnifications ranging from 1× to 20× mounted on a motorized rotating turret 125, for example. The x-ray beam magnification is changed by varying the source-to-sample and the sample-to-detector distances using the motion stages. Generally, the x-ray source, sample, and detector are placed as close as the sample size will allow.

Figure 7A:
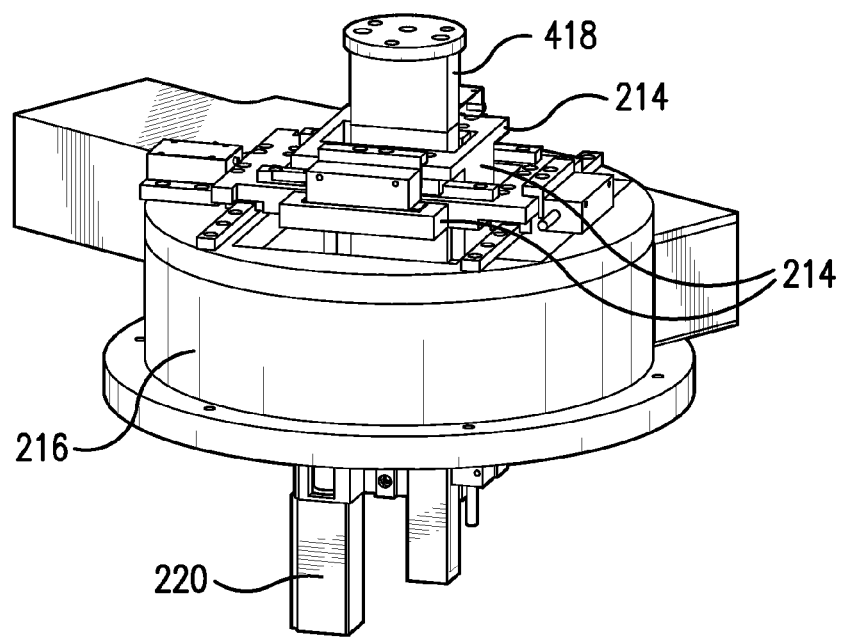
FIGS. 7a and 7b are a scale perspective and a scale top plan view of the sample carrier according to the present invention.
Figure 7B:
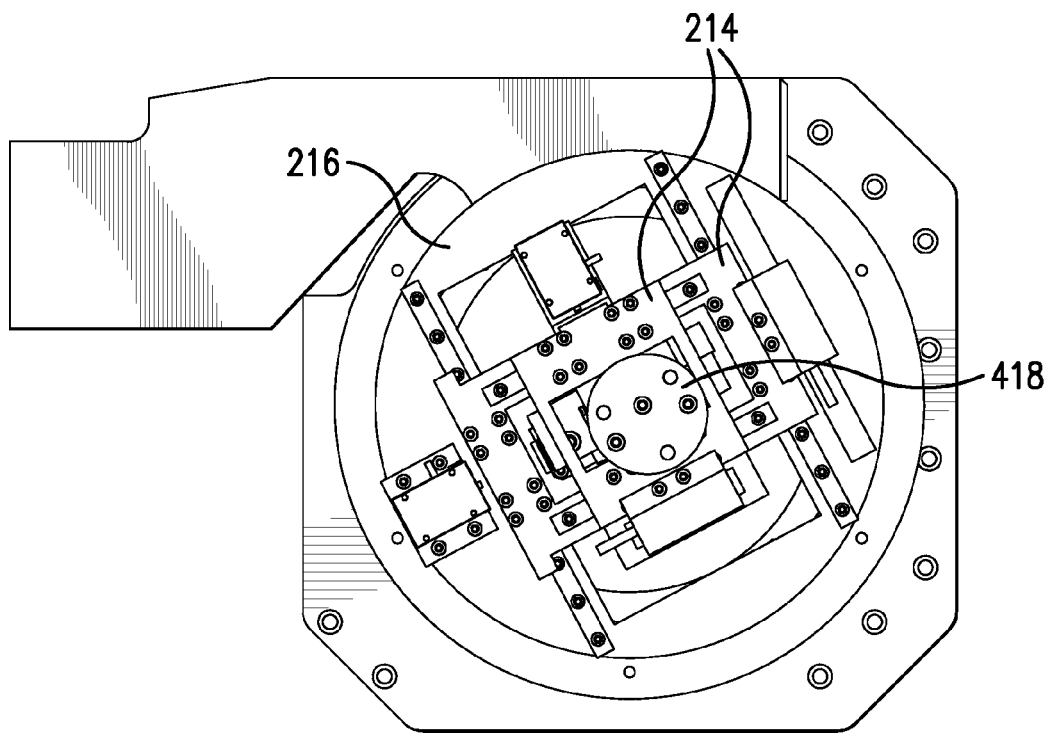

FIGS. 7a and 7b illustrate the sample stage in more detail. Specifically, the sample mount 418 is held on the x-z sample motion stage 214. This in turn is held on the sample rotation stage 216. The y-axis sample motion stage 220 further provides for the height adjustment of the sample held on the sample mount 418. By control of the x-z sample motion stage 214 and the y-axis sample motion stage 220, the alignment of the sample or target to the center of the image field is enabled to thereby create the proper conditions for tomographic imaging. Specifically, x-y-z axis motion stages are used to center the sample's region of interest at the rotation axis of the rotation stage While this invention has been particularly shown and described with references to preferred embodiments thereof, it will be understood by those skilled in the art that various changes in form and details may be made therein without departing from the scope of the invention encompassed by the appended claims.

What is claimed is:

1. An x ray imaging system, comprising:
    a projection x ray stage including:
        an x ray source generating a diverging x ray beam; and
        a scintillator for converting the x ray beam, after interacting with a sample, into an optical signal;
    an optical stage including:
        a detector; and
        a magnification lens for imaging the optical signal of the scintillator onto the detector;
        wherein a magnification of the projection x ray stage is between 1 and 10 times and a magnification of the optical stage is 5 or greater.

2. An x ray imaging system as claimed in claim 1, wherein a spot size of the x ray source is between 1 and 10 micrometers in diameter.

3. An x ray imaging system as claimed in claim 1, wherein a magnification of the optical stage is between 5 and 50 times.

4. An x ray imaging system as claimed in claim 1, wherein a magnification of the projection x ray stage is less than 2 times.

5. An x ray imaging system as claimed in claim 1, wherein a distance between the sample and the scintillator is between 1 and 50 millimeters.

6. An x ray imaging system as claimed in claim 1, wherein a distance between the sample and the scintillator is between 1 and 10 millimeters.

7. An x ray imaging system, comprising:
    a projection x ray stage including
        an x ray source generating a diverging x ray beam; and
        a scintillator for converting the diverging x ray beam, after interacting with a sample, into an optical signal, wherein a magnification of the projection x ray stage is between 1 and 10 times; and
    a sample holder for holding and positioning the sample in proximity to the scintillator, the sample holder comprising:
        a rotation motion stage for rotating the sample in the x ray beam;
        x-y-z axis motion stages to center the sample's region of interest at the rotation axis of the rotation stage; and
        at least one z-axis motion stage for adjusting a source-to-sample distance and a sample-to-detector distance with respect to the rotation motion stage and the x-y-z axis motion stages.

8. An x ray imaging system as claimed in claim 7, wherein the z-axis motion stage moves the rotation motion stage relative to a bench holding the imaging system.

9. An x ray imaging system as claimed in claim 7, further comprising a source motion stage for moving the source in a direction perpendicular to an axis of the x ray beam.

10. An x ray imaging system as claimed in claim 7, further comprising a y-axis sample motion stage for adjusting a vertical height of the sample in the x ray beam.

11. An x ray imaging system as claimed in claim 7, further comprising an optical stage including:
    a detector; and
    an optical magnification lens for imaging light from the scintillator onto the detector.

12. An x ray imaging system as claimed in claim 7, wherein a distance between the sample and the scintillator is between 1 and 50 millimeters.

13. An x ray imaging system as claimed in claim 7, wherein a distance between the sample and the scintillator is between 1 and 10 millimeters.

14. An x ray imaging system as claimed in claim 7, wherein a magnification of the projection x ray stage is less than 2 times.

15. An x ray imaging system as claimed in claim 7, further comprising an optical stage for magnifying the optical signal with a magnification of 5 or greater.

* * * * *